US00PP12631P2

(12) United States Plant Patent
Lariza et al.

(10) Patent No.: US PP12,631 P2
(45) Date of Patent: May 21, 2002

(54) PEAR TREE NAMED 'BANJO'

(76) Inventors: Francisco T. Lariza; Donald H. Lariza; Leota E. Lariza, all of 1070 Eastside Rd., Hood River, OR (US) 97031

( * ) Notice: Subject to any disclaimer, the term of this patent is extended or adjusted under 35 U.S.C. 154(b) by 0 days.

(21) Appl. No.: 09/500,141

(22) Filed: Feb. 8, 2000

(51) Int. Cl.[7] ..... A01H 5/00
(52) U.S. Cl. ..... Plt./176
(58) Field of Search ..... Plt./176

*Primary Examiner*—Bruce R. Campell
*Assistant Examiner*—Susan B. McCormick
(74) *Attorney, Agent, or Firm*—Chernoff, Vilhauer, McClung & Stenzel, LLP

(57) ABSTRACT

A new variety of pear tree discovered as a whole tree mutation. The new variety appears similar to the 'd'Anjou' pear tree but has larger leaves, shorter stems, and a different color of one-year-old wood. The date of full bloom of the new variety is 5 to 6 days later than the 'd'Anjou' tree. The fruit of the new variety has a finish that is cleaner, smoother and free of russet when compared with the finish of the 'd'Anjou' pear. The fruit of the new variety is quite edible right off to the tree, while that of the 'd'Anjou' is not.

4 Drawing Sheets

BACKGROUND AND SUMMARY OF THE INVENTION

The 'Banjo' pear (*Pyrus communis L.*) is a new, smooth skinned, very attractive cultivar with very little or no russet. This pear, unlike most pears, ripens on the tree, stores into late December and early January and has a unique shape. This new invention, which is a whole tree mutation, also has different leaf characteristics, time of bloom, time of leaf emergence and color of the one year old wood.

The 'Banjo' pear was discovered in 1987 as a whole tree mutation in a mixed orchard of 'Beurre d'Anjou' (*Pyrus communis L.*), not patented, 'Bartlett' (*Pyrus communis L.*), not patented, and 'Buerre Bosc' (*Pyrus communis L.*) not patented. The original tree, located on the Eastside Road near Hood River, Oreg., was found in between old trees that had been inter-planted in 1975 and 1976 with some of the above mentioned cultivars.

Wood from the original tree was top worked (grafted) into a young 'Columbia Red d'Anjou' (*Pyrus communis L.*) (U.S. Plant Pat. No. 6,194) tree in 1994 and is now bearing fruit. Trees propagated at the direction of the inventors are now bearing some fruit.

THE PLANT DIFFERENCES

The new cultivar grows and looks much like a 'd'Anjou' tree with an upright, spreading growth habit. The original tree lacked typical vigor for some reason but the young trees are growing well with excellent new growth and a healthy appearance. As mentioned above there are three distinguishing characteristics in the appearance of the plant.

1. The leaf size is larger on the 'Banjo' tree than on a 'd'Anjou' tree and the leaf stem is shorter when 100 leaves were measured. Measurements of the leaf are shown in the detailed description.

2. The color of the one year old wood is olive brown (4E5) on the 'Banjo' tree, olive green (2F6) on the 'd'Anjou' tree and hazel (6E8) on the 'Bartlett' tree. (See detailed description for color references).

3. Bloom data indicates that the date of bloom of the 'Banjo' tree is one to two days later than the 'Bartlett' tree and 5 to 6 days later than that of the 'd'Anjou' tree. Full bloom date for 2001 for the 'd'Anjou' tree was April 19, for the 'Bartlett' tree it was April 23 and for 'Banjo' and 'Bosc' was April 25. Temperatures in the Hood RIver Valley were cool until Apr. 23, 2001, when the weather turned quite warm.

THE FRUIT DIFFERENCES

The 'Banjo' fruit is more similar to the 'd'Anjou' fruit than it is to a 'Bartlett' or 'Bosc' fruit. The ripening characteristics and color change, however, are more similar to the 'Bartlett'. The differences in the appearance of the two fruits, 'Banjo' and 'd'Anjou,' include the following six points.

1. The 'Banjo' fruit ripens ten to fifteen days before 'd'Anjou.' From the chart below and from our experience in 1999 to 2000, it appears that the fruit could have been picked earlier than was done in 1997. From the 1997 data, the pressures were consistently higher on the 'd'Anjou' fruit than on the 'Banjo' fruit. Sugars were similar but starches were higher on the 'Banjo' fruit than on the 'D'Anjou,' as it should be on riper fruit.

| Pick | Date | Press. lbs. 'Banjo' | Sugar % 'Banjo' | Starch 'Banjo' |
|---|---|---|---|---|
| 1st | 8/26/97 | 12.4 | — | — |
| 2nd | 9/2/97 | 11.2 | — | 3.0 |
| 3rd | 9/5/97 | 10.4 | 11 | — |

Picking dates and pressures for 'Banjo' in 2000 were 1st picked fruit, Aug. 21, 2000 and 12.1 pounds, 2nd picked, Aug. 30, 2000 and 10.77 pounds, 3rd picked fruit, Sep. 5, 2000 and 9.26 pounds.

3. The 'Banjo' fruit is cleaner, smoother and free of russet when compared with the finish of the 'd'Anjou' pear. The skin has a waxy finish that, unlike the 'd'Anjou,' turns yellow (2A6) as the fruit ripens.

4. It appears that the 'Banjo' fruit is quite edible off the tree. This is not true with the 'd'Anjou' fruit which requires preripening in order to have acceptable eating quality.

5. While the interior quality of the 'Banjo' fruit is good after ripening, the smooth buttery texture of the 'd'Anjou' fruit is superior.

6. The shape of the two fruits appears to be different. The 'Banjo' fruit is longer, the width is narrower, and the stem length is longer than the 'd'Anjou' fruit. See detailed description.

7. The old 'Banjo' tree, because of its lack of vigor, has smaller fruit size than the 'd'Anjou' but the younger 'Banjo' trees have larger fruit more similar in size to the fruit of the 'd'Anjou.' For more information on fruit size see detailed description.

8. The fruit storage life has not been fully determined, but it appears that the fruit can be stored until January, while the 'd'Anjou' fruit can be stored well into June, in controlled atmosphere (CA) storage. Data collected by technicians at the Oregon State University Mid-Columbia Agriculture Research and Extension Center (MCAREC) in Hood River, from first year of storage showed the following information.

Sampled on Nov. 12, 1997, and evaluated according to maturity chart used at MCAREC.

| Pick | Date | Pressure | Scald | Browning | Flavor |
|---|---|---|---|---|---|
| 1st | 8/26/97 | 10.1 lbs | None | None | Very Good |
| 2nd | 9/2/97 | 12.5 lbs | None | None | Good |
| | | Sampled on January 12, 1998 | | | |
| 1st | 8/26/97 | 8.9 lbs | Slight | 1 of 5 | Acceptable |
| 2nd | 9/2/97 | 7.1 lbs | Some | 1 of 5 | Acceptable |
| | | Sampled on March 10, 1998 | | | |
| 1st | 8/26/97 | 7.3 lbs | Severe | 3 of 5 | Acceptable |
| 2nd | 9/2/97 | 6.3 lbs | Severe | Severe | Overripe |

The overall appearance of the fruit observed at the November 12 and January 12 evaluations was very good. From this data it appears that 'Banjo' fruit, under regular of common storage, keeps well into January. None of the fruit was treated with Ethoxyquin for scald control or a fungicide for rot control.

9. The 2000 evaluation showed that fruit picket on 8/3/00 (2nd pick) and evaluated on 11/4/00 were of excellent quality. Pressures averaged 2.46 pounds, extractable juices averaged 56.33 (100 g/FW), soluble solids averaged 13.5% and titratable acids averaged 2.82 meq/100 ml juice. No fruit exhibited scald, russet or internal browning. The fruit was juicy, smooth, had good flavor and the overall evaluation was very good.

DETAILED DESCRIPTION OF THE INVENTION

Figure 1:
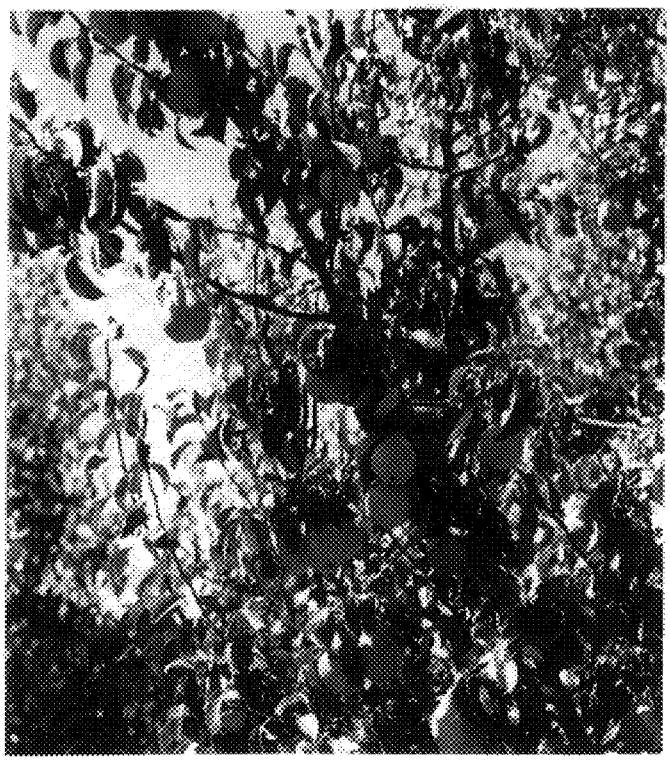
FIG. 1 shows a fruit bearing branch of the subject variety.
Figure 2:
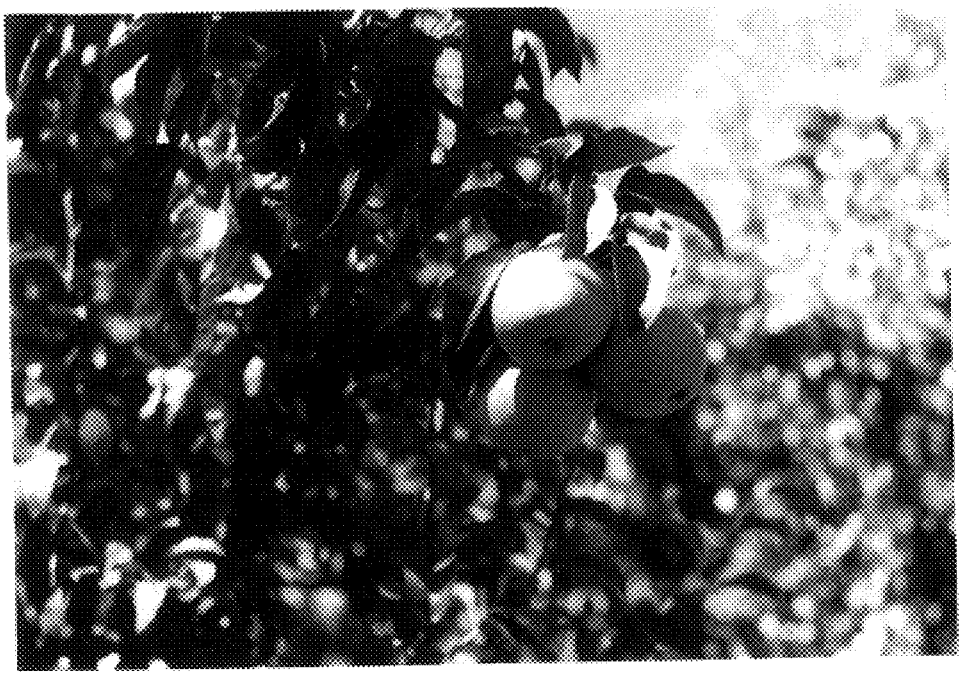
FIG. 2 shows another fruit bearing branch of the subject variety.
Figure 3:
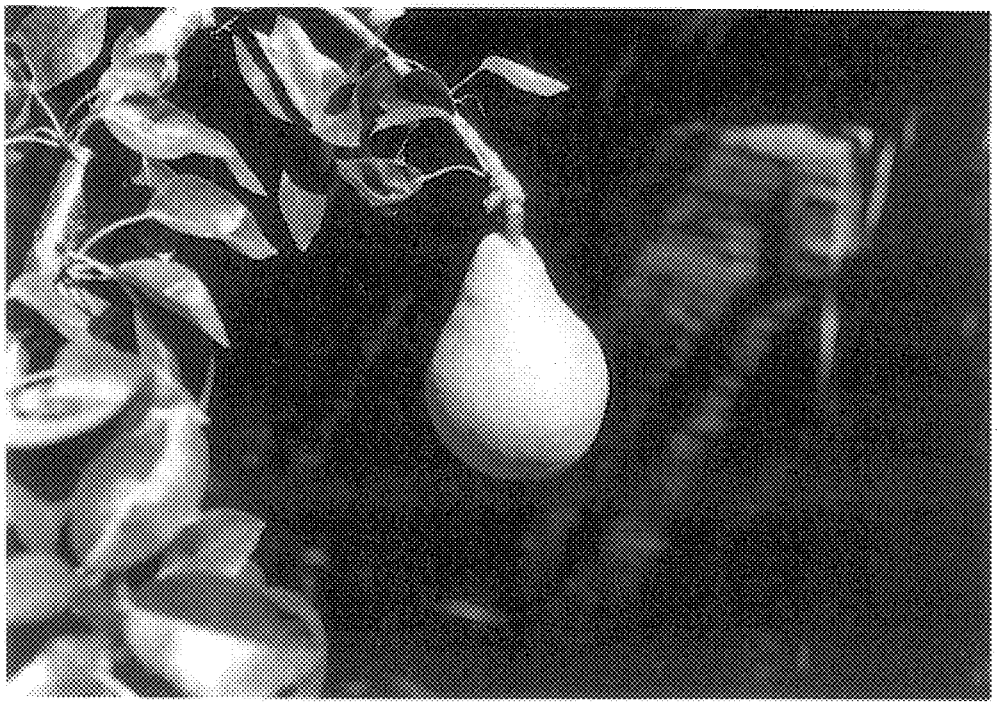
FIG. 3 shows the fruit of the subject variety.
Figure 4:
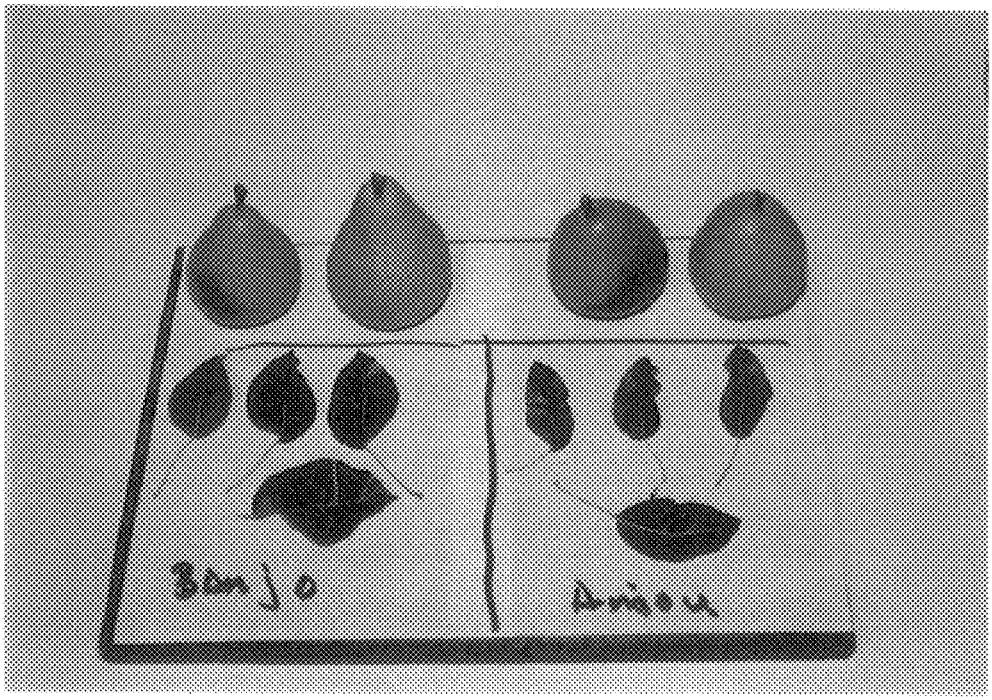
FIG. 4 shows the fruit and foliage of the subject variety on the left and the fruit and foliage of the 'd'Anjou' pear on the right.
Figure 5:
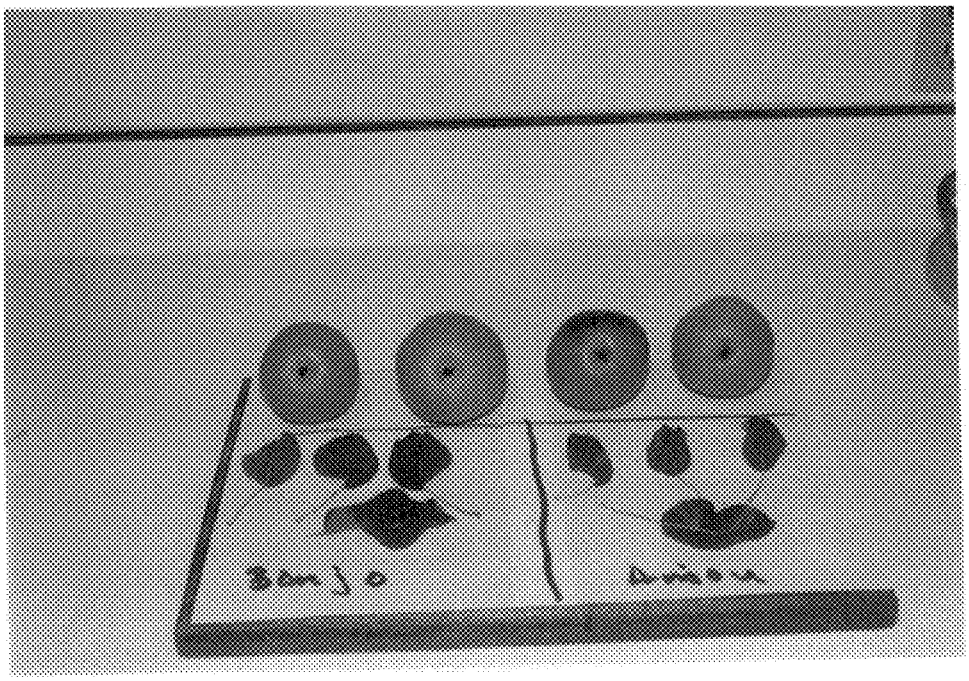
FIG. 5 shows the fruit and foliage of the subject variety on the left and the fruit and foliage of the 'd'Anjou' pear on the right.
Figure 6:
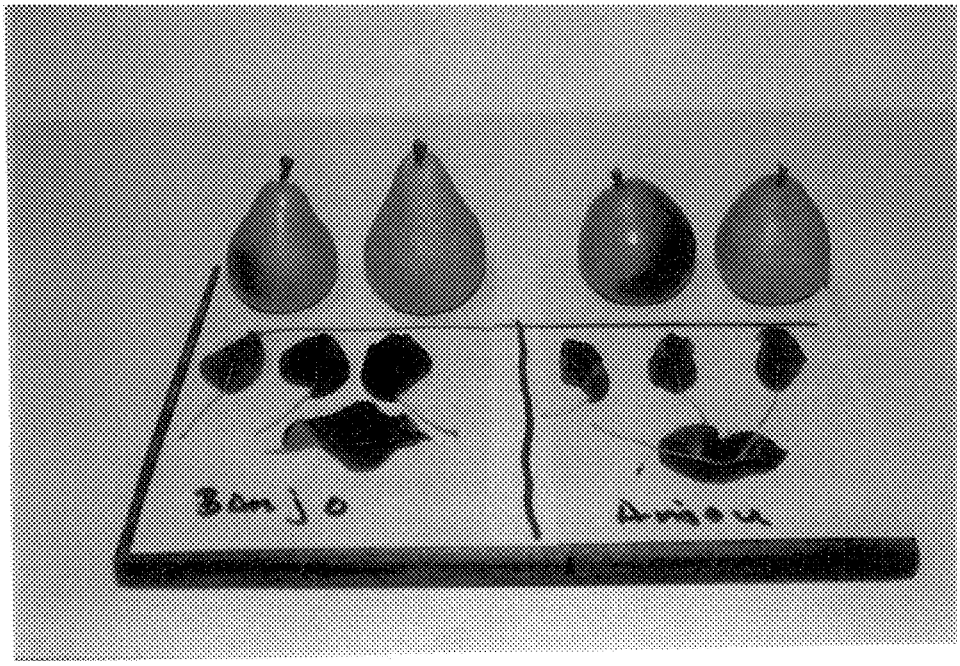
FIG. 6 shows the fruit and foliage of the subject variety on the left and the fruit and foliage of the 'd'Anjou' pear on the right.
Figure 7:
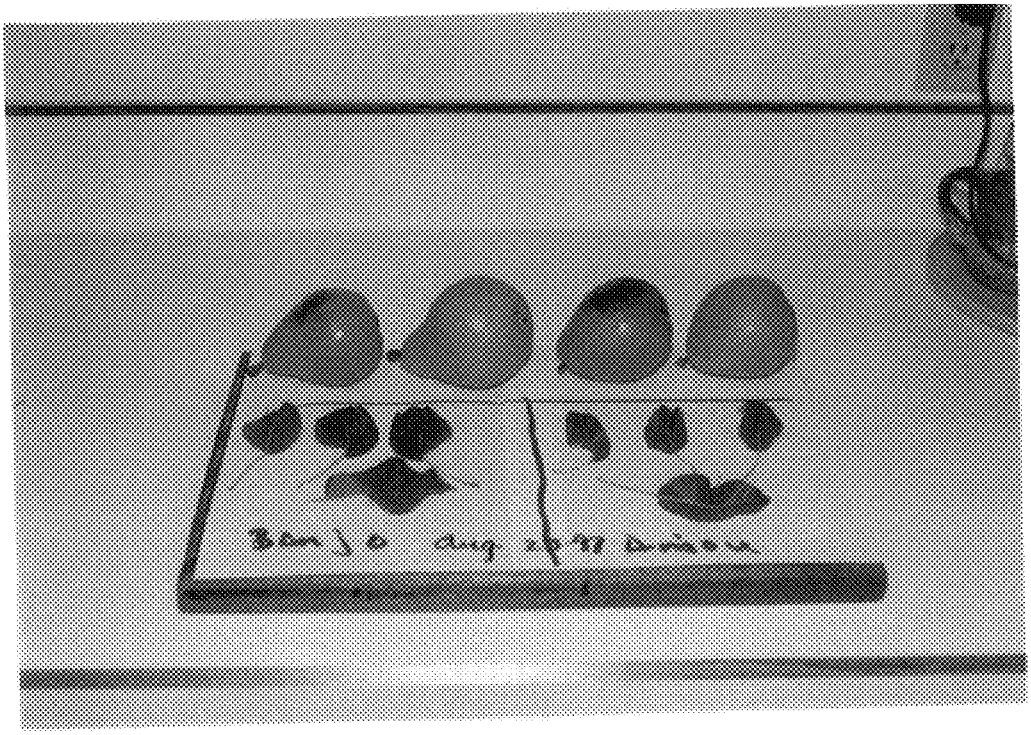
FIG. 7 shows the fruit and foliage of the subject variety on the left and the fruit and foliage of the 'd'Anjou' pear on the right.

Technology is in accordance with "Modern Systemic Pomology" by Dr. Quentin Zielinski, Professor of Horticulture at Oregon State University, and "How to Identify Plants", by H. D. Harrington, Professor of Botany and Curator of the Herbarium at Colorado State University. Color references are to the Methuen Handbook of Color by A. Kornerup and J. H. Wanscher.

Tree:

*Size.*—Slightly smaller than 'd'Anjou,' similar to 'Bartlett'; diameter of the 'Banjo' tree — 11 to 12 feet; height — 14 feet.

*Vigor.*—Moderately vigorous.

*Form.*—Somewhat spreading, upright.

*Growth.*—Moderate.

*Hardiness.*—Hardy.

*Production.*—Productive.

*Bearing.*—One year out of seven, the parent tree had a light crop.

*Trunk.*—Form: upright. Size: old tree, diameter at 30 cm from ground — 16.3 cm; young trees — 7.9 cm. Texture: medium, smooth.

*Branches.*—Color: yellowish brown (5E4). Size: old tree: main: 1st 5 leaders, average diameter — 3.91 cm. young tree: main: 1st 5 leaders, average diameter — 3.01 cm. Lateral: spreading in zigzag pattern. Branchlets: long with internodes. Color of one year old wood: olive brown (4E5). Lenticels Color: dark brown (7F8). Number per square inch: approximately 20–30. Texture: Raised, conspicuous. Size: varied.

*Leaves.*—Size: length — 7.99 cm. Width — 4.29 cm. Petiole: Length: 2.76 cm. Diameter: 1 mm. Color of petiole: greyish — green (28C6). Form: ovate, symmetrical. Apex: medium acute. Base: broadly rounded. Thickness: thin to medium. Pubescence: some hairs early, glabrate, then glabrous. Texture: smooth and leathery. Margin: finely serrated. Color: topside — deep green (27E8); underside — greyish green (28D7). Leaf buds: form — obtuse, pointed. Leaf scars: prominent.

*Flowers.*—Blooming period: first, Apr. 16, 1997— full, Apr. 20, 1997; first, Apr. 19, 2000— full, Apr. 24, 2000; first, Apr. 19, 2001— full, Apr. 25, 2001. Size: width of opened flower — 41 mm. Pistil length: 13 mm. Style length: 9 mm. Filament: 8 mm. Pedicel: Length: 27 mm. Diameter: 1–2 mm. Petals: Length: 19.6 mm. Width: 10.5 mm. Color: grayish violet (7E). Number of petals: 5. Apex: mostly obtuse, some slightly acute. Base: cunate. Margin: entire. Texture: no hairs, glabrous. FLower bud: mixed. Size: diameter — 4.3 mm. Color: olive brown (4E5). Shape: conical, plump, free.

*Fruit.*—Date of first picking: in Hood River, Oreg. about 8/21/00. Date of last picking: in Hood River, Oreg. about 9/5/00. Retention: no pre-harvest drop observed. Size: slightly smaller than 'd'Anjou,' average width, 2.81 inches in diameter and average weight, 0.49 lbs.; 'Banjo' average width, 2.7 inches diameter and average weight, 0.44 lbs. Form: ovate, pyriform. Stem, small fruit stage; Color: greyish-green (28C7). Diameter: 2.2 mm. cavity: wide, shallow, slight russett. Calyx: small, partly closed, recurved. Lobes: persistent, united at base. Basin: narrow, shallow, smooth, rounded. Sepals: Number: 5. Color: fruit side — Greyish red (9B5). calyx side — Greyish green (1C6). Skin: glabrous, medium thick. Texture: tender, smooth, waxy. Color: changes as fruit matures from yellowish green (29A6) to primrose yellow (2A6). Dots: as fruit matures the small inconspicuous dots disappear.

*Flesh.*—Color: white. Texture: tender, juicy, fine-grained. Flavor: sweet, sub-acid, flat. Eating quality: very good. Core: distant, closed. Core lines: meeting. Calyx tube: urn-shaped.

*Seed.*—Size: small, 10 in number. Shape: acuminate. Color: dark brown (8F5).

*Fruit use.*—Fresh market, dessert.

*Keeping quality.*—Excellent to late December, early January.

*Shipping quality.*—Undetermined as no fruit has been shipped commercially.

*Resistance to insects or mildew.*—Does not appear to be more or less tolerant or susceptible to pests. No winter damage observed on old or young trees.

We claim:

1. A new and distinct variety of pear tree, referred to as the Banjo cultivar, substantially as shown and described herein, characterized by its fruit finish being clean, smooth and free of russet.

* * * * *

UNITED STATES PATENT AND TRADEMARK OFFICE

CERTIFICATE OF CORRECTION

PATENT NO. : PP 12,631 P2
DATED : May 21, 2002
INVENTOR(S) : Frank Lariza

It is certified that error appears in the above-identified patent and that said Letters Patent is hereby corrected as shown below:

Column 1,
Line 21, delete the comma (,) in "6,194."

Column 2,
Line 4, delete "RIver" and insert -- River --

Column 3,
Line 40, delete "picket" and insert -- picked --

Signed and Sealed this

Eleventh Day of November, 2003

JAMES E. ROGAN
*Director of the United States Patent and Trademark Office*